United States Patent [19]
Yoshikawa et al.

[11] Patent Number: 5,916,770
[45] Date of Patent: Jun. 29, 1999

[54] MACROPHAGE STIMULATING PROTEIN VARIANT AND METHOD FOR PRODUCING THE SAME

[75] Inventors: Wataru Yoshikawa; Manabu Shimonishi; Junko Iwamoto; Toyohiro Takehara; Michio Hagiya, all of Ohtsu, Japan

[73] Assignee: Toyo Boseki Kabushiki Kaisha, Japan

[21] Appl. No.: 08/666,082

[22] Filed: Jun. 19, 1996

[30] Foreign Application Priority Data

Jun. 20, 1995 [JP] Japan ................................. 7-153309

[51] Int. Cl.$^6$ .......................... C12N 15/19; C12N 15/00; C12N 15/63; C07K 14/52
[52] U.S. Cl. ...................... 435/69.5; 435/69.1; 435/69.6; 435/252.3; 435/254.11; 435/320.1; 435/325; 435/360; 435/365.1; 530/350; 530/351; 530/380; 530/395; 530/403; 536/23.1; 536/23.5; 935/6; 935/10; 935/22; 935/27; 935/31; 935/32; 935/68; 935/70
[58] Field of Search .................................. 435/69.1, 69.5, 435/69.6, 240.1, 240.2, 252.3, 254.11, 320.1, 325, 360, 365.1; 530/350, 351, 380, 395, 403; 536/23.1, 23.5; 935/6, 10, 22, 27, 31, 32, 68, 70, 72

[56] References Cited

U.S. PATENT DOCUMENTS

| | | | |
|---|---|---|---|
| 5,219,991 | 6/1993 | Leonard et al. | 530/351 |
| 5,315,000 | 5/1994 | Degen | 536/23.5 |
| 5,446,020 | 8/1995 | Andy et al. | 514/3 |

OTHER PUBLICATIONS

Exp. Cell. Res., vol. 102, pp. 434–438, 1976. A Serum Protein that Stimulates Macrophage Movement, Chemotaxis and Spreading, E.J. Leonard and Alison Skeel.

The Journal of Experimental Medicine, vol. 173, pp. 1227–1234, 1991. Macrophage Stimulating Protein: Purification, Partial Amino Acid Sequence, and Cellular Activity, Alison Skeel, Teizo Yoshimura, Stephen D. Showalter, Shuji Tanaka, Ettore Appella, and Edward J. Leonard.

Biochemistry, vol. 30, No. 40, pp. 9768–9780, 1991. Characterization of the DNF15S2 Locus on Human Chromosome 3: Identification of a Gene Coding for Four Kringle Domains with Homology to Hepatocyte Growth Factor, Su Han, Lorie A. Stuart, and Sandra J. Friezner Degen.

The Journal of Biological Chemistry, vol. 268, No. 21, pp. 15461–15468, 1993. Cloning, Sequencing, and Expression of Human Macrophage Stimulating Protein (MSP, MST1) Confirms MSP as a Member of the Family of Kringle Proteins and Locates the MSP Gene on Chromosome 3, Teizo Yoshimura, Naoya Yuhki, Ming–Hai Wang, Alison Skeel, and Edward J. Leonard, pp. 15461–15468, Jul. 25, 1993.

The Journal of Biological Chemistry, vol. 269, No. 5, pp. 3436–3440, 1994. Proteolytic Conversion of Single Chain Precursor Macrophage–stimulating Protein to a Biologically Active Heterodimer by Contact Enzymes of The Coagulation Cascade, Ming–Hai Wang, Teizo Yoshimura, Alison Skeel, and Edward J. Leonard.

Biochemistry, vol. 27, No. 21, pp. 8097–8105, 1988. The Structure of Rat Mast Cell Protease II at 1.9–Å Resolution, Stephen J. Remington, Richard G. Woodbury, Ross A. Reynolds, Brian W. Matthews, and Hans Neurath.

Biochemistry, vol. 23, No. 26, pp. 6570–6575, 1984. Critical Evaluation of Comparative Model Building of Streptomyces Griseus Trypsin, Randy J. Read, Gary D. Brayer, Lubomir Jurášek, and Michael N. G. James, pp. 6570–6575, 1984.

Journal of Leukocyte Biology, vol. 54, pp. 289–295, 1993. Antibodies to Machrophage Stimulating Protein (MSP): Specificity, Epitope interactions, and immunoassay of MSP in Human Serum, Ming–Hai Wang, Alison Skeel, Teizo Yoshimura, Terry D. Copeland, Kazuyasu Sakaguchi, and Edward J. Leonard.

*Primary Examiner*—Ronald B. Schwardron
*Attorney, Agent, or Firm*—Levdig, Voit & Mayer Ltd.

[57] ABSTRACT

The present invention relates to a macrophage stimulating protein wherein a cysteine residue at position 672 from the N-terminus in the amino acid sequence of native form macrophage stimulating protein is deleted or substituted by another amino acid residue, e.g., an alanine residue; a DNA fragment encoding the protein; a recombinant vector including the DNA fragment; a host cell transformed with the recombinant vector; and a method for culturing the transformed host cell and recovering a macrophage stimulating protein variant from the cultured host cell.

14 Claims, 5 Drawing Sheets

Native form MSP

C672A variant

Eluted fractions

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 711 amino acids
      (B) TYPE: amino acid
      (D) TOPOLOGY: linear (ii) MOLECULE TYPE: protein (xi) SEQUENCE DESCRIPTION: SEQ ID NO:1:

```
Met Gly Trp Leu Pro Leu Leu Leu Leu Thr Gln Tyr Leu Gly Val
 1               5                  10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
                35                  40                  45

Asp Val Ala Asp Ala Glu Glu Cys Ala Gly Arg Cys Gly Pro Leu Met
        50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
                100                 105                 110

Asn Asn Gly Val Gly Tyr Arg Gly Thr Met Ala Thr Thr Val Gly Gly
            115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
                180                 185                 190

Trp Cys Asn Gly Glu Glu Tyr Arg Gly Ala Val Asp Arg Thr Glu Ser
                195                 200                 205

Gly Arg Glu Cys Gln Arg Trp Asp Leu Gln His Pro His Gln His Pro
    210                 215                 220
```

-continued

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
            245                 250                 255

Gln Ile Glu Arg Glu Phe Cys Asp Leu Pro Arg Cys Gly Ser Glu Ala
        260                 265                 270

Gln Pro Arg Gln Glu Ala Thr Val Ser Cys Phe Arg Gly Lys Gly
    275                 280                 285

Glu Gly Tyr Arg Gly Thr Ala Asn Thr Thr Thr Ala Gly Val Pro Cys
290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350

Ala Phe Cys Tyr Gln Ile Arg Arg Cys Thr Asp Asp Val Arg Pro Gln
        355                 360                 365

Asp Cys Tyr His Gly Ala Gly Glu Gln Tyr Arg Gly Thr Val Ser Lys
    370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
        435                 440                 445

Ala Asp Asp Gln Pro Pro Ser Ile Leu Asp Pro Pro Asp Gln Val Gln
    450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
            500                 505                 510

Lys Glu Gln Trp Ile Leu Thr Ala Arg Gln Cys Phe Ser Ser Cys His
        515                 520                 525

Met Pro Leu Thr Gly Tyr Glu Val Trp Leu Gly Thr Leu Phe Gln Asn
    530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
            580                 585                 590

Trp Tyr Val Val Pro Pro Gly Thr Lys Cys Glu Ile Ala Gly Trp Gly
        595                 600                 605

Glu Thr Lys Gly Thr Gly Asn Asp Thr Val Leu Asn Val Ala Leu Leu
    610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala

```
                        645                 650                 655
Cys Glu Gly Asp Tyr Gly Gly Pro Leu Ala Cys Phe Thr His Asn Cys
            660                 665                 670

Trp Val Leu Glu Gly Ile Ile Ile Pro Asn Arg Val Cys Ala Arg Ser
            675                 680                 685

Arg Trp Pro Ala Val Phe Thr Arg Val Ser Val Phe Val Asp Trp Ile
    690                 695                 700

His Lys Val Met Arg Leu Gly
705                 710

(2) INFORMATION FOR SEQ ID NO:2:

(i) SEQUENCE CHARACTERISTICS:
        (A) LENGTH: 2216 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Human (ix) FEATURE:
        (A) NAME/KEY: sig peptide
        (B) LOCATION: 1..54

(ix) FEATURE:
        (A) NAME/KEY: CDS
        (B) LOCATION: 1..2133

(xi) SEQUENCE DESCRIPTION: SEQ ID NO:2:

ATG GGG TGG CTC CCA CTC CTG CTG CTT CTG ACT CAA TAC TTA GGG GTC         48
Met Gly Trp Leu Pro Leu Leu Leu Leu Leu Thr Gln Tyr Leu Gly Val
 1               5                  10                  15

CCT GGG CAG CGC TCG CCA TTG AAT GAC TTC CAA GTG CTC CGG GGC ACA         96
Pro Gly Gln Arg Ser Pro Leu Asn Asp Phe Gln Val Leu Arg Gly Thr
                20                  25                  30

GAG CTA CAG CAC CTG CTA CAT GCG GTG GTG CCC GGG CCT TGG CAG GAG        144
Glu Leu Gln His Leu Leu His Ala Val Val Pro Gly Pro Trp Gln Glu
            35                  40                  45

GAT GTG GCA GAT GCT GAA GAG TGT GCT GGT CGC TGT GGG CCC TTA ATG        192
Asp Val Ala Asp Ala Glu Glu Cys Ala Gly Arg Cys Gly Pro Leu Met
    50                  55                  60

GAC TGC CGG GCC TTC CAC TAC AAC GTG AGC AGC CAT GGT TGC CAA CTG        240
Asp Cys Arg Ala Phe His Tyr Asn Val Ser Ser His Gly Cys Gln Leu
65                  70                  75                  80

CTG CCA TGG ACT CAA CAC TCG CCC CAC ACG AGG CTG CGG CGT TCT GGG        288
Leu Pro Trp Thr Gln His Ser Pro His Thr Arg Leu Arg Arg Ser Gly
                85                  90                  95

CGC TGT GAC CTC TTC CAG AAG AAA GAC TAC GTA CGG ACC TGC ATC ATG        336
Arg Cys Asp Leu Phe Gln Lys Lys Asp Tyr Val Arg Thr Cys Ile Met
                100                 105                 110

AAC AAT GGG GTT GGG TAC CGG GGC ACC ATG GCC ACG ACC GTG GGT GGC        384
Asn Asn Gly Val Gly Tyr Arg Gly Thr Met Ala Thr Thr Val Gly Gly
            115                 120                 125

CTG CCC TGC CAG GCT TGG AGC CAC AAG TTC CCG AAT GAT CAC AAG TAC        432
Leu Pro Cys Gln Ala Trp Ser His Lys Phe Pro Asn Asp His Lys Tyr
    130                 135                 140

ACG CCC ACT CTC CGG AAT GGC CTG GAA GAG AAC TTC TGC CGT AAC CCT        480
Thr Pro Thr Leu Arg Asn Gly Leu Glu Glu Asn Phe Cys Arg Asn Pro
145                 150                 145                 160

GAT GGC GAC CCC GGA GGT CCT TGG TGC TAC ACA ACA GAC CCT GCT GTG        528
Asp Gly Asp Pro Gly Gly Pro Trp Cys Tyr Thr Thr Asp Pro Ala Val
```

-continued

```
                    165                 170                 175
CGC TTC CAG AGC TGC GGC ATC AAA TCC TGC CGG GAG GCC GCG TGT GTC      576
Arg Phe Gln Ser Cys Gly Ile Lys Ser Cys Arg Glu Ala Ala Cys Val
                180                                 190

TGG TGC AAT GGC GAG GAA TAC CGC GGC GCG GTA GAC CGC ACG GAG TCA      624
Trp Cys Asn Gly Glu Glu Tyr Arg Gly Ala Val Asp Arg Thr Glu Ser
                            200

GGG CGC GAG TGC CAG CGC TGG GAT CTT CAG CAC CCG CAC CAG CAC CCC      672
Gly Arg Glu Cys Gln Arg Trp Asp Leu Gln His Pro His Gln His Pro
            210                                 220

TTC GAG CCG GGC AAG TTC CTC GAC CAA GGT CTG GAC GAC AAC TAT TGC      720
Phe Glu Pro Gly Lys Phe Leu Asp Gln Gly Leu Asp Asp Asn Tyr Cys
                        230                                 240

CGG AAT CCT GAC GGC TCC GAG CGG CCA TGG TGC TAC ACT ACG GAT CCG      768
Arg Asn Pro Asp Gly Ser Glu Arg Pro Trp Cys Tyr Thr Thr Asp Pro
                                    250

CAG ATC GAG CGA GAG TTC TGT GAC CTC CCC CGC TGC GGG TCC GAG GCA      816
Gln Ile Glu Arg Glu Phe Cys Asp Leu Pro Arg Cys Gly Ser Glu Ala
                    260                                 270

CAG CCC CGC CAA GAG GCC ACA ACT GTC AGC TGC TTC CGC GGG AAG GGT      864
Gln Pro Arg Gln Glu Ala Thr Thr Val Ser Cys Phe Arg Gly Lys Gly
                                280

GAG GGC TAC CGG GGC ACA GCC AAT ACC ACC ACT GCG GGC GTA CCT TGC      912
Glu Gly Tyr Arg Gly Thr Ala Asn Thr Thr Thr Ala Gly Val Pro Cys
290                                             300

CAG CGT TGG GAC GCG CAA ATC CCT CAT CAG CAC CGA TTT ACG CCA GAA      960
Gln Arg Trp Asp Ala Gln Ile Pro His Gln His Arg Phe Thr Pro Glu
                            310                                 320

AAA TAC GCG TGC AAA GAC CTT CGG GAG AAC TTC TGC CGG AAC CCC GAC     1008
Lys Tyr Ala Cys Lys Asp Leu Arg Glu Asn Phe Cys Arg Asn Pro Asp
                                        330

GGC TCA GAG GCG CCC TGG TGC TTC ACA CTG CGG CCC GGC ATG CGC GCG     1056
Gly Ser Glu Ala Pro Trp Cys Phe Thr Leu Arg Pro Gly Met Arg Ala
                340                                 350

GCC TTT TGC TAC CAG ATC CGG CGT TGT ACA GAC GAC GTG CGG CCC CAG     1104
Ala Phe Cys Tyr Gln Ile Arg Arg Cys Thr Asp Asp Val Arg Pro Gln
                            360

GAC TGC TAC CAC GGC GCA GGG GAG CAG TAC CGC GGC ACG GTC AGC AAG     1152
Asp Cys Tyr His Gly Ala Gly Glu Gln Tyr Arg Gly Thr Val Ser Lys
370                                             380

ACC CGC AAG GGT GTC CAG TGC CAG CGC TGG TCC GCT GAG ACG CCG CAC     1200
Thr Arg Lys Gly Val Gln Cys Gln Arg Trp Ser Ala Glu Thr Pro His
                        390                                 400

AAG CCG CAG TTC ACG TTT ACC TCC GAA CCG CAT GCA CAA CTG GAG GAG     1248
Lys Pro Gln Phe Thr Phe Thr Ser Glu Pro His Ala Gln Leu Glu Glu
                    405                 410                 415

AAC TTC TGC CGG AAC CCA GAT GGG GAT AGC CAT GGG CCC TGG TGC TAC     1296
Asn Phe Cys Arg Asn Pro Asp Gly Asp Ser His Gly Pro Trp Cys Tyr
                420                 425                 430

ACG ATG GAC CCA AGG ACC CCA TTC GAC TAC TGT GCC CTG CGA CGC TGC     1344
Thr Met Asp Pro Arg Thr Pro Phe Asp Tyr Cys Ala Leu Arg Arg Cys
            435                 440                 445

GCT GAT GAC CAG CCG CCA TCA ATC CTG GAC CCC CCA GAC CAG GTG CAG     1392
Ala Asp Asp Gln Pro Pro Ser Ile Leu Asp Pro Pro Asp Gln Val Gln
450                 455                 460

TTT GAG AAG TGT GGC AAG AGG GTG GAT CGG CTG GAT CAG CGG CGT TCC     1440
Phe Glu Lys Cys Gly Lys Arg Val Asp Arg Leu Asp Gln Arg Arg Ser
465                 470                 475                 480

AAG CTG CGC GTG GTT GGG GGC CAT CCG GGC AAC TCA CCC TGG ACA GTC     1488
Lys Leu Arg Val Val Gly Gly His Pro Gly Asn Ser Pro Trp Thr Val
```

-continued

|  |  |  |  |  |  | 485 |  |  |  | 490 |  |  |  | 495 |  |  |
|---|---|---|---|---|---|---|---|---|---|---|---|---|---|---|---|---|

```
AGC TTG CGG AAT CGG CAG GGC CAG CAT TTC TGC GGG GGG TCT CTA GTG     1536
Ser Leu Arg Asn Arg Gln Gly Gln His Phe Cys Gly Gly Ser Leu Val
            500                 505                 510

AAG GAG CAG TGG ATA CTG ACT GCC CGG CAG TGC TTC TCC TCC TGC CAT     1584
Lys Glu Gln Trp Ile Leu Thr Ala Arg Gln Cys Phe Ser Ser Cys His
            515                 520                 525

ATG CCT CTC ACG GGC TAT GAG GTA TGG TTG GGC ACC CTG TTC CAG AAC     1632
Met Pro Leu Thr Gly Tyr Glu Val Trp Leu Gly Thr Leu Phe Gln Asn
        530                 535                 540

CCA CAG CAT GGA GAG CCA AGC CTA CAG CGG GTC CCA GTA GCC AAG ATG     1680
Pro Gln His Gly Glu Pro Ser Leu Gln Arg Val Pro Val Ala Lys Met
545                 550                 555                 560

GTG TGT GGG CCC TCA GGC TCC CAG CTT GTC CTG CTC AAG CTG GAG AGA     1728
Val Cys Gly Pro Ser Gly Ser Gln Leu Val Leu Leu Lys Leu Glu Arg
                565                 570                 575

TCT GTG ACC CTG AAC CAG CGC GTG GCC CTG ATC TGC CTG CCC CCT GAA     1776
Ser Val Thr Leu Asn Gln Arg Val Ala Leu Ile Cys Leu Pro Pro Glu
            580                 585                 590

TGG TAT GTG GTG CCT CCA GGG ACC AAG TGT GAG ATT GCA GGC TGG GGT     1824
Trp Tyr Val Val Pro Pro Gly Thr Lys Cys Glu Ile Ala Gly Trp Gly
            595                 600                 605

GAG ACC AAA GGT ACG GGT AAT GAC ACA GTC CTA AAT GTG GCC TTG CTG     1872
Glu Thr Lys Gly Thr Gly Asn Asp Thr Val Leu Asn Val Ala Leu Leu
610                 615                 620

AAT GTC ATC TCC AAC CAG GAG TGT AAC ATC AAG CAC CGA GGA CGT GTG     1920
Asn Val Ile Ser Asn Gln Glu Cys Asn Ile Lys His Arg Gly Arg Val
625                 630                 635                 640

CGT GAG AGT GAG ATG TGC ACT GAG GGA CTG TTG GCC CCT GTG GGG GCC     1968
Arg Glu Ser Glu Met Cys Thr Glu Gly Leu Leu Ala Pro Val Gly Ala
                645                 650                 655

TGT GAG GGT GAC TAC GGG GGC CCA CTT GCC TGC TTT ACC CAC AAC TGC     2016
Cys Glu Gly Asp Tyr Gly Gly Pro Leu Ala Cys Phe Thr His Asn Cys
                660                 665                 670

TGG GTC CTG GAA GGA ATT ATA ATC CCC AAC CGA GTA TGC GCA AGG TCC     2064
Trp Val Leu Glu Gly Ile Ile Ile Pro Asn Arg Val Cys Ala Arg Ser
            675                 680                 685

CGC TGG CCA GCT GTC TTC ACG CGT GTC TCT GTG TTT GTG GAC TGG ATT     2112
Arg Trp Pro Ala Val Phe Thr Arg Val Ser Val Phe Val Asp Trp Ile
690                 695                 700

CAC AAG GTC ATG AGA CTG GGT TAGGCCCAGC CTTGATGCCA TATGCCTTGG        2163
His Lys Val Met Arg Leu Gly
705                 710

GGAGGACAAA ACTTCTTGTC AGACATAAAG CCATGTTTCC TCTTTATGCC TGT          2216

(2) INFORMATION FOR SEQ ID NO:3:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:3:

TGCCTGCTTT ACCCACAACG CCTGGGTCCT GGAAGGAATT                         40

(2) INFORMATION FOR SEQ ID NO:4:

(i) SEQUENCE CHARACTERISTICS:
        (A) LENGTH: 20 base pairs
```

(B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:4:

TGGCCATTGA ATGACTTCCA                                              20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:5:

TGATCATTCG GGAACTTGTG                                              20

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(ix) FEATURE:
        (A) NAME/KEY: CDS
        (B) LOCATION: 2..40

(xi) SEQUENCE DESCRIPTION: SEQ ID NO:6:

T GCC TGC TTT ACC CAC AAC GCC TGG GTC CTG GAA GGA ATT              40
  Ala Cys Phe Thr His Asn Ala Trp Val Leu Glu Gly Ile
  1           5                   10

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ala Cys Phe Thr His Asn Ala Trp Val Leu Glu Gly Ile
    1           5                   10

MACROPHAGE STIMULATING PROTEIN VARIANT AND METHOD FOR PRODUCING THE SAME

BACKGROUND OF THE INVENTION

1. Field of the Invention

The present invention relates to a macrophage stimulating protein variant wherein a cysteine residue at position 672 from the N-terminus in the amino acid sequence of macrophage stimulating protein is deleted or substituted by another amino acid residue; a DNA fragment encoding the variant; a recombinant vector including the DNA fragment; a host cell transformed with the recombinant vector; and a method for producing the macrophage stimulating protein variant by culturing the transformed host cell.

2. Description of the Related Art

Macrophage stimulating protein (hereinafter, referred to as MSP) enhances phagocytosis, stimulates chemotaxis, and induces morphological changes of, for example, murine resident peritoneal macrophages (Leonard et al., Exp. Cell. Res., 102, 434 (1976); Skeel et al., J. Exp. Med., 173, 1227 (1991)). Because MSP has the ability to activate macrophages, which belong to phagocytes, it is expected that MSP may serve as a preventive pharmaceutical agent for infectious disease.

MSP was first isolated and purified from human serum, and its partial amino acid sequence was then determined (Skeel et al., J. Exp. Med., 173, 1227 (1991); Leonard et al., U.S. Pat. No. 5,219,991).

A nucleotide sequence of cDNA independently isolated from a hepatocarcinoma cell line HepG2, encoding an amino acid sequence homologous to that of hepatocyte growth factor, which was designated as a hepatocyte growth factor-like protein (HGF-like protein), was reported (Han et al., Biochemistry, 30, 9768 (1991); Degen et al., U.S. Pat. No. 5,315,000). Thereafter, it was reported that an amino acid sequence encoded by cDNA which was cloned using the partial amino acid sequence of MSP was completely identical with that of HGF-like protein (Yoshimura et al., J. Biol. Chem., 268 15461 (1993)). Furthermore, by observing that a culture supernatant of COS cells transfected with an expression vector for the HGF-like protein-encoding cDNA had MSP activity, it was confirmed that MSP is identical with HGF-like protein.

MSP is a glycoprotein composed of 693 amino acids excluding signal sequence. MSP is secreted as a single chain inactive form (hereinafter, referred to as pro-MSP). Pro-MSP is specifically cleaved between Arg (493) and Val (494) with an enzyme such as human kallikrein and converted into a two-chain active form MSP (Wang et al., J. Biol. Chem., 269, 3436 (1994)). Native MSP purified from human serum is in a two-chain form The native MSP migrates as a single band with a molecular weight of about 70 Kd on SDS electrophoresis under non-reducing condition, while it is separated into an α-chain band with a molecular weight of about 47 Kd and a β-chain band with a molecular weight of about 22 Kd under reducing condition. More specifically, the α-chain (Gln19 to Arg493) and the β-chain (Val494 to Gly711) of MSP are cross-linked through a disulfide bond. It is considered that a disulfide bond is formed between Cys (468) and Cys (588) in the amino acid sequence of MSP through the comparative study with the amino acid sequences of hepatocyte growth factor and plasminogen.

SUMMARY OF THE INVENTION

According to one aspect of the present invention, an MSP variant is provided, wherein a cysteine residue in an amino acid sequence of MSP is deleted or substituted by another amino acid residue In one embodiment of the present invention, the cysteine residue is at position 672 from the N-terminus of SEQ ID NO: 1.

In another embodiment of the present invention, the cysteine residue is deleted.

In another embodiment of the present invention, the cysteine residue is substituted by another amino acid residue.

Alternatively, a DNA fragment encoding an MSP variant is provided, wherein a cysteine residue in an amino acid sequence of MSP is deleted or substituted by another amino acid residue.

In one embodiment of the present invention, the cysteine residue is at position 672 from the N-terminus of SEQ ID NO: 1.

In another embodiment of the present invention, the cysteine residue is deleted.

In another embodiment of the present invention, nucleotides at positions 2014 to 2016 of SEQ ID NO: 2 are deleted.

In another embodiment of the present invention, another amino acid is an alanine residue.

In another embodiment of the present invention, nucleotides at positions 2014 to 2016 of SEQ ID NO: 2 are substituted by other nucleotides.

In another embodiment of the present invention, the other nucleotides are GCC, GCU, GCA or GCG.

Alternatively, a recombinant vector including the above-mentioned DNA fragment is provided.

Alternatively, a host cell transformed with the above-mentioned recombinant vector is provided.

According to another aspect of the present invention, a method for producing an MSP variant is provided, which includes the steps of: transforming a host cell with a recombinant vector including a DNA fragment encoding an MSP variant; culturing the transformed host cells; and recovering the MSP variant from the culture, wherein a cysteine residue in an amino acid sequence of MSP is deleted or substituted by another amino acid residue.

In one embodiment of the present invention, the cysteine residue is deleted.

In another embodiment of the present invention, the cysteine residue is substituted by another amino acid residue.

Thus, according to the present invention, a method for producing a native form MSP in large quantity by using a recombinant DNA technique is provided. More specifically, the invention described herein advantageously affords for providing: (1) an MSP variant wherein a cysteine residue at position 672 from the N-terminus of the native MSP is deleted or substituted by another amino acid residue (e.g., alanine residue); (2) a DNA fragment encoding the MSP variant; (3) a recombinant vector including the DNA fragment; (4) a host cell transformed with the recombinant vector; and (5) a method for culturing the transformed host cell and recovering the MSP variant from the culture.

When MSP is produced using cDNA encoding the native sequence, disulfide bonds in some recombinant proteins are formed between the cysteine residues which are different from those in native MSP. Therefore, this recombinant protein contains a large quantity of component without macrophage stimulating activity. On the other hand, according to the present invention, the MSP variant has a disulfide bond between the same cysteine residues as those of native MSP, resulting in the production of recombinant protein having macrophage stimulating activity of large quantity The MSP variant of the present invention can solve the problem of the formation of unusual disulfide bonds between the cysteine residues in recombinantly expressed native form MSP. Such undesirable disulfide bonds result in the production of free chains without physiological activity in large quantity. The MSP variant of the present invention enables the production of a two-chain active form recombinant MSP having the same physiological activity as that of human native MSP efficiently and at low cost.

These and other advantages of the present invention will become apparent to those skilled in the art upon reading and understanding the following detailed description with reference to the accompanying figures.

DESCRIPTION OF THEE PREFERRED EMBODIMENTS

The inventors initially constructed a transformant which expresses native form MSP from cDNA encoding the native sequence using a CHO cell as a host to provide a recombinant MSP protein having physiological (macrophage stimulating) activity in large quantity at a low cost. However, the inventors found that liberated α-chain and β-chain, as well as two-chain active form MSP, were generated in a culture supernatant of transfected CHO cells. This suggested that some of the MSP recombinant protein did not form a disulfide bond between the α-chain and the β-chain. Furthermore, the liberated α-chain and β-chain did not activate macrophages.

As described above, a disulfide bond between the α-chain and the β-chain was not formed in some recombinant MSP protein. In recent years, it has been known that various proteins are involved in a process of folding a biologically synthesized polypeptide chain in a cell. These proteins include protein disulfide-isomerase (PDI), peptidyl prolyl cis-trans isomerase, and stress proteins collectively called chaperone The folding of recombinant protein is achieved in cooperation with these chaperone-like proteins in host cells. Therefore, it is advantageous to select a host cell which has closer characteristics to naturally occurring MSP-producing cells in order to allow the recombinant protein to be folded in the same way as in the native protein. However, the recombinant protein may be folded differently or form alternative disulfide bonds due to the limitation in selecting host cells.

Figure 1:
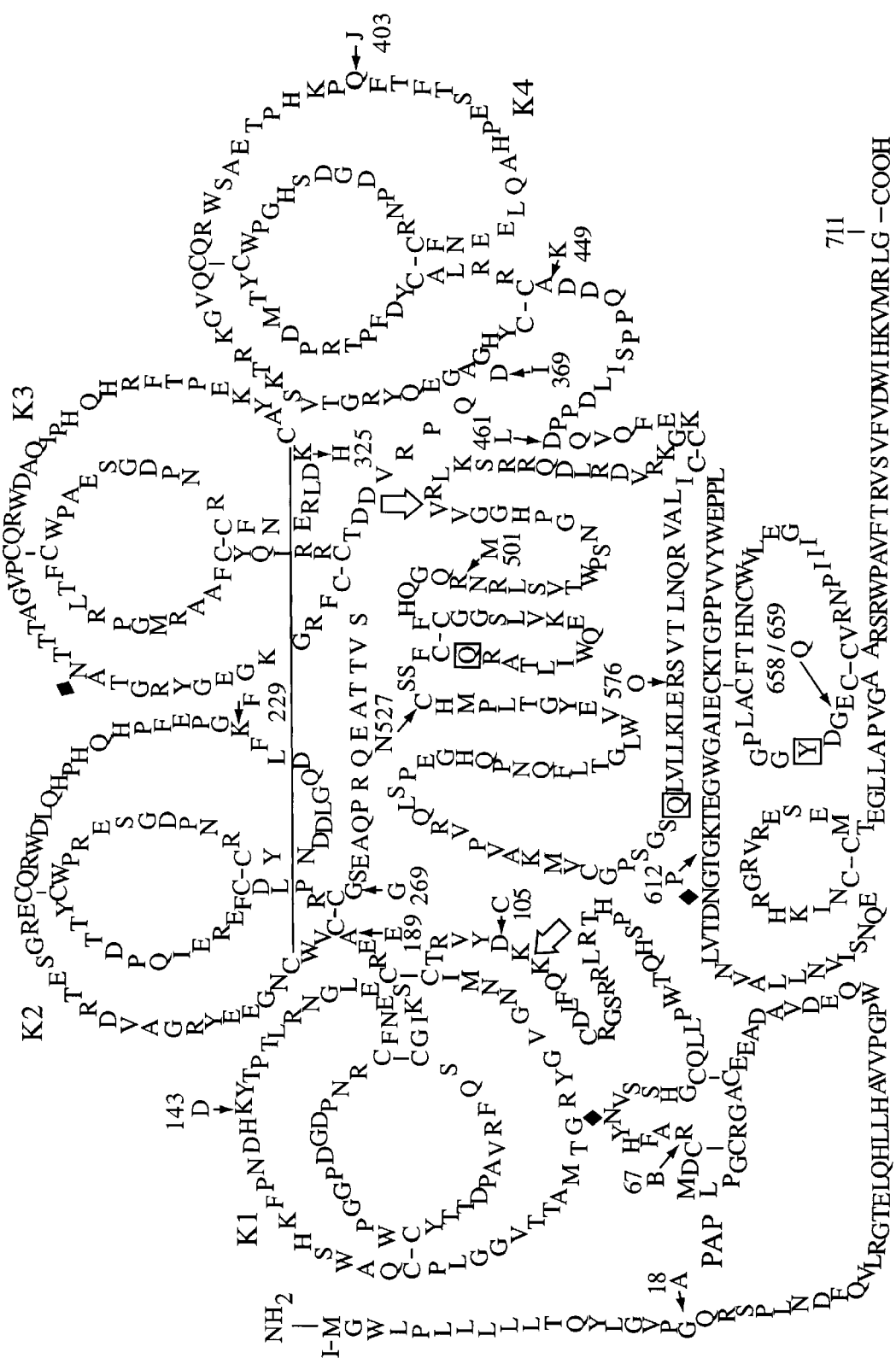
FIG. 1 illustrates disulfide bonds between cysteine residues of MSP assumed from plasminogen.
Figure 2:
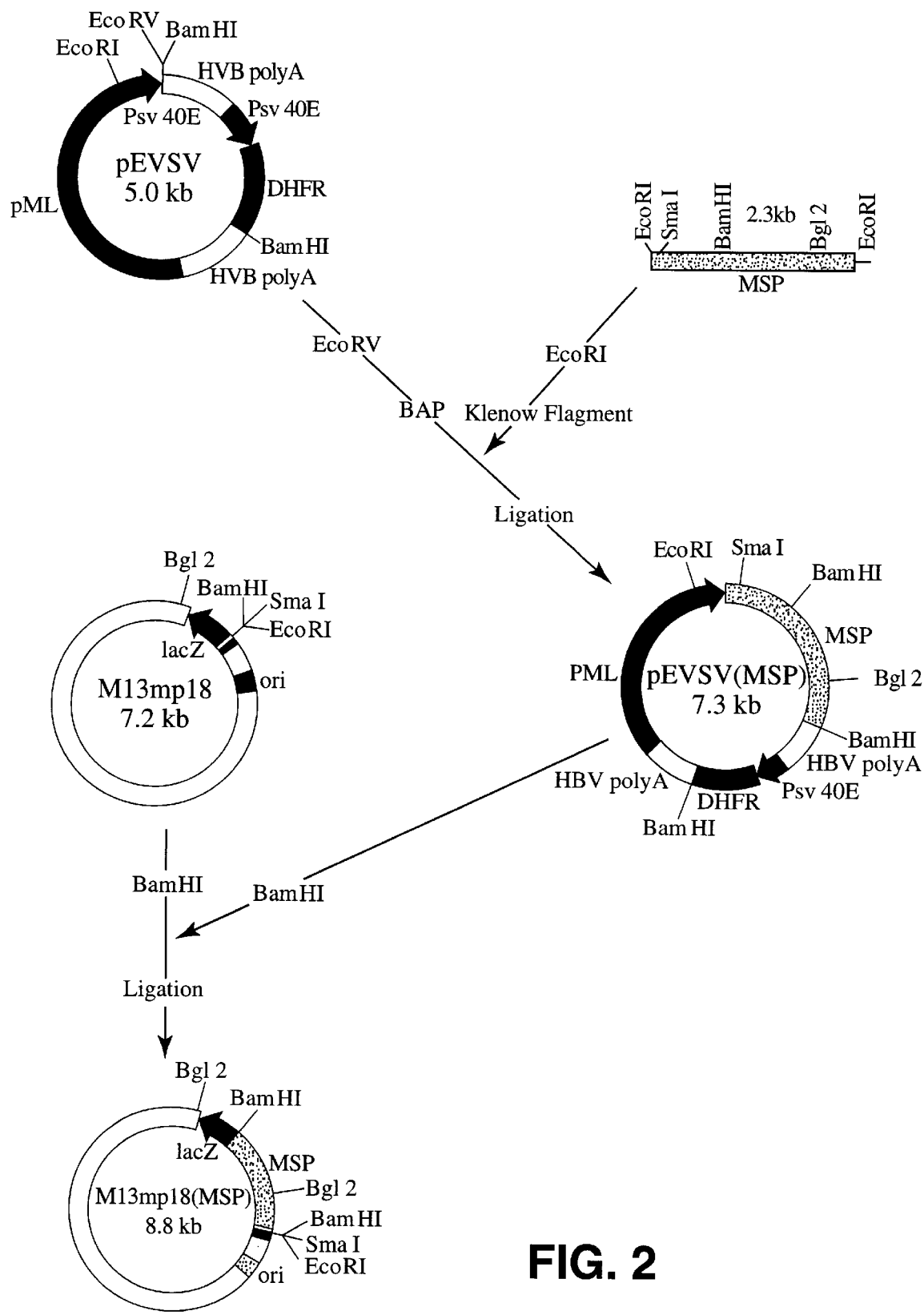
FIG. 2 illustrates the scheme for the construction of plasmid pEVSV (MSP) as well as M13mp18 (MSP) used as a template for mutagenesis in the Examples.
Figure 3:
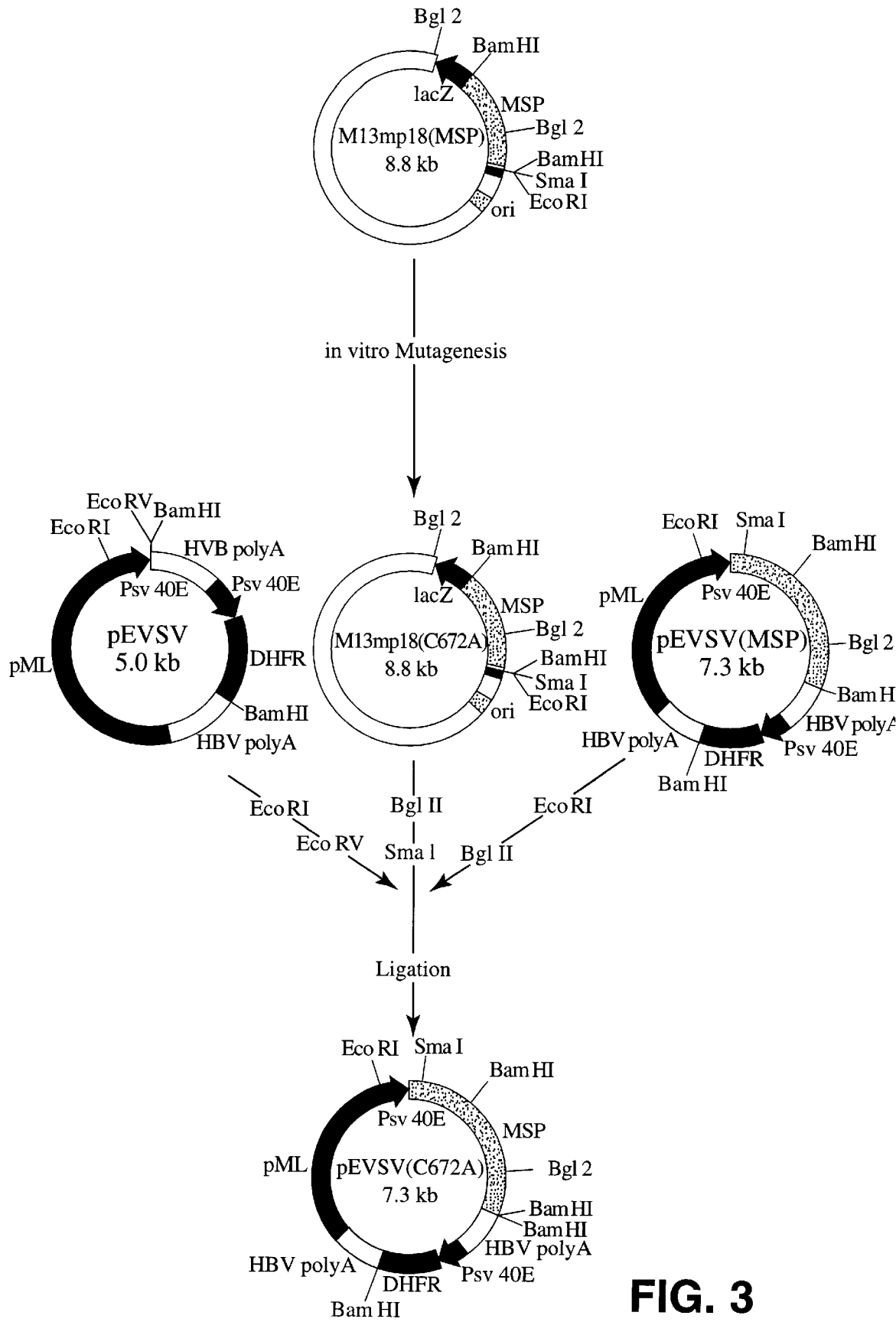
FIG. 3 illustrates the scheme for the construction of pEVSV (mMSP) in the Examples.

The inventors thoroughly studied the amino acid sequence of MSP with respect to disulfide bonds in the recombinant MSP protein. The amino acid sequence of MSP consists of a kringle domain and a serine protease-like domain as do plasminogen and HGF. Each domain has homology in the amino acid sequences among these proteins. MSP has 44 cysteine residues in total, of which 40 cysteine residues are conserved at positions similar to those in the amino acid sequence of plasminogen. From the detailed description by Han et al., Biochemistry, 30, 9708 (1991), most combinations of cysteines within MSP which form disulfide bonds can be determined according to the amino acid sequence of plasminogen. These combinations are 56 and 78; 60 and 66; 110 and 186; 131 and 169; 157 and 181; 191 and 268; 212 and 251; 240 and 263; 283 and 361; 304 and 343; 332 and 355; 370 and 448; 391 and 431; 419 and 443; 507 and 523; 602 and 667; 632 and 646; 657 and 686; 194 and 324; and 468 and 588 (see FIG. 1).

However, 4 cysteines, i.e., Cys(98), Cys(527), Cys(562), and Cys(672) are not conserved in amino acid sequences of plasminogen or its related proteins. Therefore, it is not clear whether these cysteines form a disulfide bond or remain in a free state. The formation of a disulfide bond between one of these four cysteines and Cys(468) or Cys(588) may prevent formation of the proper disulfide bonds between Cys(468) and Cys(588) which cross-link the α-chain to the β-chain.

The inventors further studied the above-mentioned possibility in view of the findings relating to the stereostructure of a protein. For disulfide bond formation in protein molecules, side chains of two cysteine residues to be bonded should be spatially close to each other. X-ray crystal structure analysis for three-dimensional stereostructure on MSP has not been conducted. However, the β-chain of MSP is a serine protease-like domain, whose amino acid sequences are homologous to a number of related proteins of which the X-ray crystal structures have already been determined (Stephen et al., Biochemistry, 27, 8097 (1988); Randy et al., Biochemistry, 23, 6570 (1984)). The three-dimensional stereostructures of serine protease related proteins are known to be well conserved with each other. Based on the crystal structure of bovine trypsin, which is a serine protease, the respective distances among Cys(527), Cys($56^2$), Cys(588), and Cys(672) in the β-chain of MSP were estimated. As a result, Cys(672) was estimated to be spatially close to Cys(588). When a disulfide bond is formed between Cys (672) and Cys(588), the disulfide bond between Cys(588) and Cys(468) is not formed. Therefore, the recombinant MSP protein is cleaved between amino acid residues at positions 493 and 494, and liberated into inactive α-chain and β-chain components rather than becoming a two-chain active form of MSP.

Based on the above-mentioned findings, the inventors employed a recombinant DNA technique known as site-directed mutagenesis in order to introduce mutation into a cysteine residue at position 672 of MSP. Consequently, we found that a two-chain active form of recombinant MSP was produced efficiently to achieve the present invention.

More specifically, the present invention relates to an MSP variant wherein a cysteine residue in an amino acid sequence of an MSP is deleted or substituted by another amino acid residue.

The present invention also relates to an MSP variant wherein the cysteine residue at position 672 from the N-terminus of SEQ ID NO: 1 is deleted or substituted by another amino acid residue.

The present invention also relates to an MSP variant wherein the cysteine residue at position 672 from the N-terminus in SEQ ID NO: 1 is deleted.

The present invention also relates to an MSP variant wherein the cysteine residue at position 672 from the N-terminus in SEQ ID NO: 1 is substituted by another amino acid residue.

In one embodiment of the present invention, the cysteine residue at position 672 from the N-terminus of SEQ ID NO: 1 is substituted by an alanine residue.

The present invention relates to a DNA fragment encoding an MSP variant wherein a cysteine residue at position 672 from the N-terminus of SEQ ID NO: 1 is deleted.

One embodiment of the present invention is a DNA fragment encoding an MSP variant wherein nucleotides at positions 2014 to 2016 of SEQ ID NO: 2 are deleted. SEQ ID NO: 2 is a nucleotide sequence encoding MSP of SEQ ID NO: 1 The cysteine residue at position 672 from the N-terminus of SEQ ID NO: 1 is encoded by the nucleotides at positions 2014 to 2016 of SEQ ID NO: 2.

The present invention also relates to a DNA fragment encoding an MSP variant wherein the cysteine residue at position 672 from the N-terminus of SEQ ID NO: 1 is substituted by another amino acid residue.

One embodiment of the present invention is a DNA fragment encoding an MSP variant wherein the cysteine residue at position 672 from the N-terminus of SEQ ID NO: 1 is substituted by an alanine residue.

The present invention relates to a recombinant vector comprising a DNA fragment encoding an MSP variant wherein a cysteine residue at position 672 from the N-terminus of SEQ ID NO: 1 is deleted.

The present invention also relates to a recombinant vector comprising a DNA fragment encoding an MSP variant wherein a cysteine residue at position 672 from the N-terminus of SEQ ID NO: 1 is substituted by another amino acid residue.

The present invention relates to a host cell transformed with a recombinant vector including a DNA fragment encoding an MSP variant wherein a cysteine residue at position 672 from the N-terminus of SEQ ID NO: 1 is deleted.

The present invention also relates to a host cell transformed with a recombinant vector including a DNA fragment encoding an MSP variant wherein a cysteine residue at position 672 from the N-terminus of SEQ ID NO: 1 is substituted by another amino acid residue.

The present invention relates to a method for producing an MSP variant, comprising the steps of: transforming a host cell with a recombinant vector comprising a DNA fragment encoding an MSP variant wherein a cysteine residue at position 672 from the N-terminus of SEQ ID NO: 1 is deleted; culturing the transformed host cells; and recovering an MSP variant from the culture.

The present invention relates to a method for producing an MSP variant, comprising the steps of: transforming a host cell with a recombinant vector comprising a DNA fragment encoding an MSP variant wherein a cysteine residue at position 672 from the N-terminus of SEQ ID NO: 1 is substituted by another amino acid residue; culturing the transformed host cells; and recovering an MSP variant from the culture.

The MSP variant of the present invention refers to a protein wherein a cysteine residue at position 672 in an amino acid sequence of human MSP (SEQ ID NO: 1) is deleted or substituted by another amino acid residue.

Preferably, the cysteine residue is substituted by one amino acid residue other than a cysteine residue, such as alanine, glycine, and serine.

The DNA fragment encoding the MSP variant of the present invention has nucleotides at positions 2014 to 2016 of a nucleotide sequence encoding MSP of SEQ ID NO: 1 being deleted or substituted by nucleotides encoding another amino acid sequence. For the substitution at positions 2014 to 2016, at least one nucleotide among those may be substituted so as to encode another amino acid residue.

As for DNA encoding the MSP variant, MSP encoding cDNA obtained recombinantly from reverse transcribed mRNA, DNA encoding human MSP obtained from genomic DNA, and the like can be used. Although any MSP encoding DNAs can be used as MSP cDNA, DNA of SEQ ID NO: 2 is preferred.

MSP cDNA can be prepared as follows. Total RNA is first extracted from a culture cell or a human tissue by the acid guanidine thiocyanate-phenol-chloroform extraction method (Analytical Biochemistry, 162, 156–159 (1987)), and the extract is subjected to an oligo-dT-cellulose column or OLIGOTEX™ DT30 (Nippon Roche K. K.) to obtain polyA+RNA. Then, single-stranded cDNA is synthesized from the polyA+RNA by using an oligo-dT-primer and reverse transcriptase. Then, double-stranded cDNA can be synthesized using RNase H and DNA polymerase I. The resulting cDNA may be inserted into a λ phage vector or the like. Packaged cDNA library can be screened for human MSP cDNA with a probe derived from human MSP. Alternatively, an appropriate PCR primer is designed from human MSP sequence to obtain human MSP cDNA by conducting PCR reaction.

In order to introduce mutation into MSP encoding DNA, commercially available kits for site-directed mutagenesis, for example, T7-GEN™ In Vitro Mutagenesis Kit (United States Biochemical corporation) can be used. More specifically, single-stranded DNA is first prepared from an MSP DNA clone. Then, a primer for the opposite strand spanning about 40 bp around the site in which mutation is to be incorporated including mutation or deletion is prepared. The primer is annealed to the single-stranded MSP DNA template. Thereafter, a complementary strand of the template is extended from the primer with T7 DNA polymerase in the presence of, for example, 5-Methyl-dCTP, and ligated to produce double-stranded circular DNA with T4 DNA ligase. Then, the template and incompletely extended strand are cleaved with MspI, HhaI, or the like. $E.$ $coli$ cells are transformed with newly synthesized remaining mutant DNA strand to obtain nucleotide sequence encoding the MSP variant.

The recombinant vector of the present invention refers to an appropriate vector, such as plasmid, in which a DNA fragment encoding the MSP variant is contained so as to be functionally expressed. Examples of the recombinant vectors include, but are not limited to, plasmids derived from $E.$ $coli,$ $Bacillus$ $subtilis,$ yeast and animal virus.

Introduction of the DNA encoding the MSP variant into vector DNA can be conducted by a conventional recombinant DNA technique, in which both the DNAs are digested with a restriction enzyme and ligated with each other with T4 DNA ligase. The ligation can also be conducted by processing the ends of the DNA fragments digested with restriction enzymes by fill-in reaction using a DNA polymerase I Klenow fragment, blunting reaction using T4DNA polymerase, or using a DNA linker.

With the vector which comprises recombinant DNA fragment having a nucleotide sequence encoding the MSP variant thus constructed, host cells are transformed. Examples of the host cells include, but are not limited to, $E.$ coli cells., *Bacillus subtilis* cells, yeast cells, and animal cells. Examples of the animal cells include, but are not limited to, simian COS-1 cells, and Chinese Hamster Ovary (CHO) cells.

The transformation of the host cells is conducted according to the method described, for example, in Methods in Enzymology, Goeddel ed., (1991), vol. 185, Academic Press, Inc. Animal cells are transformed using, for example, a lipofection method. A host cell transformed with a vector comprising recombinant DNA encoding the MSP variant thus can be obtained.

The resulting transformed host cells are cultured in a culture medium to produce the MSP variant. When transformed animal cells are cultured, an MEM medium containing about 1 to 20% of fetal bovine serum (Science, 122, 501 (1952)), an RPMI1640 medium (Journal of the American Medical Association, 199, 519 (1967)), or the like can be used. The pH of the medium is preferably about 6 to 8. The cultivation time is about 15 to 60 hours, with ventilation or stirring, if required.

EXAMPLES Hereinafter, the present invention will be described by way of illustrative examples.

Example 1
DNA cloning of human MSP

```
(5'-T GCC TGC TTT ACC CAC AAC GCC TGG GTC CTG GAA GGA ATT-3')  [SEQ ID NO: 6]
      A   C   F   T   H   N   A   W   V   L   E   G   I         [SEQ ID NO: 7]
```

A PCR reaction was conducted by using primer 1 (TGGCCATTGAATGACTTCCA)[SEQ ID NO: 4], primer 2 (TGATCATTCGGGAACTTGTG)[SEQ ID NO: 5], and Pfu DNA polymerase with mRNA derived from a Hep G2 cell line as a template. The resulting 0.36 kb fragment was subcloned into an EcoRV restriction site of pBlueScript SK+ (Stratagene). The nucleotide sequence of subcloned DNA was confirmed, and then, the inserted 0.36 kb MSP fragment was cut out with restriction enzymes EcoRI and HindIII. Then, using the fragment as a probe, $5 \times 10^5$ clones from HepG2 cDNA library (Clontech) were screened to obtain 4 positive clones. The clone (MSP9) with the longest insert of about 2.3 kb was selected, and the insert was cut out with restriction enzyme EcoRI to subclone into an EcoRI restriction site of pBlueScript SK+. The nucleotide sequence of the resulting clone (pBS(MSP9)) was confirmed to be identical with SEQ ID NO: 2.

Example 2

Alteration of MSP by substituting Cys at position 672 of native form MSP with Ala (hereinafter referred to as C672A) Incorporation of MSP cDNA into expression vector pEVSV for CHO cells The plasmid vector pBS (MSP9) bearing human MSP cDNA was first digested with restriction enzyme EcoRI to obtain a 2.3 kb DNA fragment including human MSP cDNA. The resulting DNA fragment was treated with a DNA polymerase I large fragment (Klenow fragment) to obtain a blunt-end DNA. Then, an EcoRV restriction site of pEVSV (an expression vector for CHO cells) was cleaved for DNA insertion and treated with bacterial alkaline phosphatase (BAP) in order to prevent self-ligation. The resulting vector with blunt-ends was mixed with the above-mentioned DNA fragment containing human MSP cDNA, and the two fragments were ligated with each other with T4 DNA ligase. *E. coli* JM109 was transformed with the ligated DNA, and plated onto LB plates containing ampicillin. Clones in which human MSP DNA was inserted in the correct direction downstream the SV40 early promotor were selected to obtain expression vector pEVSV (MSP) for CHO cells.

Generation of DNA encoding an MSP variant (C672A)

Expression vector pEVSV (MSP) for CHO cells was digested with restriction enzyme BamHI to obtain a 1.6 kb DNA fragment encoding the C-terminus portion of human MSP. Phage vector M13mp18 which provides single-stranded DNA was digested with restriction enzyme BamHI. The digested phage vector M13mp18 was mixed with the 1.6 kb DNA fragment, and they were ligated with each other with T4 DNA ligase. *E. coli* JM109 was transformed with the ligated DNA and plated onto H plates with *E. coli* JM109 as a lawn. A clone having the 16 kb DNA fragment for the C-terminus portion of MSP inserted in a direction in which the minus strand of the fragment would be released was selected to obtain M13mp18 (MSP). The selected clone was cultured to release single-stranded M13mp18 DNA in the phage particles containing the insert. This single-stranded DNA was purified and used as a template for introducing mutation. The single-stranded DNA so obtained contained the minus strand for the C-terminus portion of MSP.

In order to substitute a cysteine residue at position 672 of MSP with an alanine residue, oligonucleotide was synthesized Then, 5'-OH termini of 400 picomoles of the oligonucleotides were phosphorylated with T4 DNA kinase. Mutation was introduced by using 20 picomoles of the oligonucleotide thus obtained, the single-stranded M13mp18 (MSP) DNA prepared above as a template, and T7 GEN™ kit (United States Biochemical Corporation) for site-directed mutagenesis *E. coli* K802 strain (mcrB-) was transformed with the DNA thus obtained, and then, plated onto LB plates with *E. coli* JM109 strain (F') as a lawn. *E. coli* JM109 cells were infected with phages from the resulting plaques and cultured, and then, DNA was purified from the cells thus obtained. The DNA sequences of 11 clones among DNAs obtained above were confirmed. Two clones were shown to contain the introduction of mutation, and thus, clone M13mp18(C672A), in which a cysteine residue at position 672 is substituted by an alanine residue, was obtained.

Introduction of DNA encoding an MSP variant (C672A) into CHO expression vector

The expression vector pEVSV (MSP) containing MSP cDNA was digested with restriction enzymes EcoRI and BglII to obtain a 2.1 kbp DNA fragment containing the N-terminus-encoding portion of human MSP cDNA and an SV40 early promoter. Separately, M13mp18 (C672A) which had been mutagenized as described above was digested with restriction enzymes SmaI and BglII to obtain a 0.6 kbp DNA fragment containing a C-terminus-encoding portion of MSP cDNA. Then, the expression vector pEVSV was cleaved at the EcoRV cloning site and an EcoRI site immediately upstream the SV40 early promoter to obtain a 4.6 kbp DNA fragment containing DHFR-encoding DNA and the like.

Three DNA fragments thus obtained were mixed and ligated with T4 DNA ligase. The EcoRI-digested site might be ligated with the EcoRI-digested site, and the BglII-digested site might be ligated with the BglII-digested site. Moreover, both the EcoRV-digested site and the SmaI-digested site were blunt-ended so that these sites might be ligated with each other. *E. coli* JM109 was transformed with the ligated DNA and plated onto LB plates containing ampicillin. A pEVSV (C672A) clone containing an MSP variant cDNA (C672A) insert was selected.

Preparation of vector DNA for constructing a transformed host cell

*E. coli* clones containing pEVSV (C672A) or pEVSV (C672A) were cultured overnight in 40 ml of an LB medium containing 100 mg/ml of ampicillin. Plasmid DNA was prepared from the cultured cells by an alkaline extraction method. The plasmid DNA was further purified by ultracentrifugation with CsCl. The resulting plasmid DNA was used to construct recombinant cells for the production of human MSP and MSP variant (C672A) using CHO cells as a host.

Construction of transformed CHO cells

CHO cells were transformed by a lipofection method. First, $1.0 \times 10^6$ CHO cells were seeded in a ø60 mm dish and cultured for one day in αMEM medium supplemented with 10% FCS. Then, 20 µg of each of the expression plasmid DNA for human MSP or MSP variant (C672A) was dissolved in 100 µl of Opti-MEM I medium. Next, 25 µl of lipofectin solution (GIBCO) was mixed with 75 µl of serum-free Opti-MEM I medium After 100 µl of DNA solution was mixed with the lipofectin-medium mixture, the resulting mixture was allowed to stand at room temperature for 15 minutes to form a DNA-lipofectin complex. Furthermore, 1.8 ml of Opti-MEM I medium was added to the complex to give a total volume of 2 ml. Then, the whole DNA-lipofectin complex solution was added to the CHO cells in the dish, and the CHO cells were allowed to stand in a 5% $CO_2$ incubator at 37° C. for 18 to 24 hours to be transformed The cells were further cultured for one day after replacing the medium with an αMEM medium supplemented with 10% FCS. The cells containing transformed cells thus obtained were seeded in a dish or flask at an appropriate cell density to form colonies The cells were cultured in a nucleic acid-free αMEM synthetic medium supplemented with 10% FBS from which nucleic acid had been removed by dialysis The colonies were isolated by using penicillin cups. The collected colonies were expanded in the nucleic acid-free αMEM medium in 12-well culture plates Thereafter, the amounts of the human MSP and the MSP variant (C672A) in supernatants were determined by immunoassay (Wang et al., J. Leukoc. Biol., 54, 289 (1993)).

Culturing of CHO recombinant cells and purification of MSP and MSP variant (C672A)

CHO recombinant cells for MSP and MSP variant (C672A) were expanded in an RPMI medium supplemented with 10% fetal bovine serum in a T225 flask until they became confluent. The culture medium was replaced by a serum-free RPMI medium containing 50 µg/ml leupeptin in order to obtain single-chain form recombinant MSP. Culture supernatant of each recombinant cell was collected every other day, thus obtaining about 1 L of culture supernatants in total. The culture supernatants were loaded onto an anti-human MSP monoclonal antibody column. After adequately washing the column with a phosphate buffer, recombinant MSP or MSP variant (C672A) was eluted in a glycine buffer at pH 2.8. The elutes were immediately neutralized with suitable volume of 1M Tris-HCl, pH9.0. The resultant material was analyzed on SDS-PAGE. The gel was visualized by silver staining. The single-chain form MSP migrates as a single band of about 70 kd under reducing or non-reducing condition, whereas the two-chain form MSP is separated into an α-chain band of about 47 kd and a β-chain band of 22 kd under reducing condition. The recombinant MSP and MSP variant (C672A) obtained from the serum-free RPMI medium containing leupeptin migrated as a single band of about 90 kd on SDS-PAGE under reducing condition, indicating that they were single-chain form MSPs (hereinafter referred to as "pro-MSP" and "pro-C672A", respectively)

Kallikrein treatment of pro-MSP and pro-C672A

Using human kallikrein (American Diagnostica), purified pro-MSP and pro-C672A were specifically cleaved at the peptide bond between arginine at position 493 and valine at position 494. Specifically, 1 mg of human kallikrein was bound to Affi-Gel 10 columns, through which purified fractions of pro-MSP and pro-C672A were passed The respective fractions were subjected to SDS-PAGE analysis under reducing condition. Either of the pro-MSP and pro-C672A before the kallikrein treatment exhibited single bands of about 70 kd, which completely disappeared after the kallikrein treatment Afterward, bands of about 47 kd and 22 kd corresponding to the α-chain and the β-chain, respectively, were appeared That is, both pro-MSP and pro-C672A were digested by substantially 100% through the kallikrein treatment. SDS-PAGE under non-reducing condition resulted in three bands of about 70 kd, 47 kd, and 22 kd. These bands correspond to the molecular weights of two-chain form MSP, the free α-chain and the free β-chain, respectively. These species of molecules were separated using a reverse phase column to determine the ratio therebetween.

Analysis of the free α-chain and the free β-chain

Figure 4:
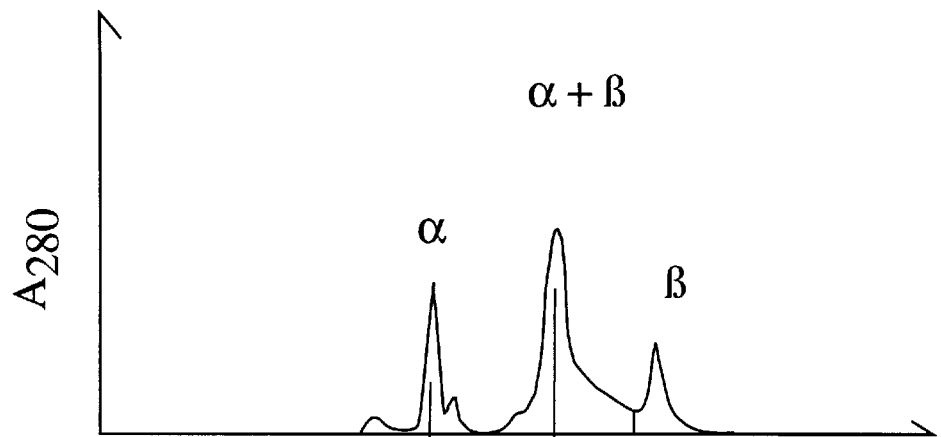
FIG. 4 illustrates elution patterns of pro-MSP (native MSP) and pro-C672A (C672A variant) analyzed on phenyl 5PW reverse-phase HPLC after treatment with kallikrein.
Figure 4:
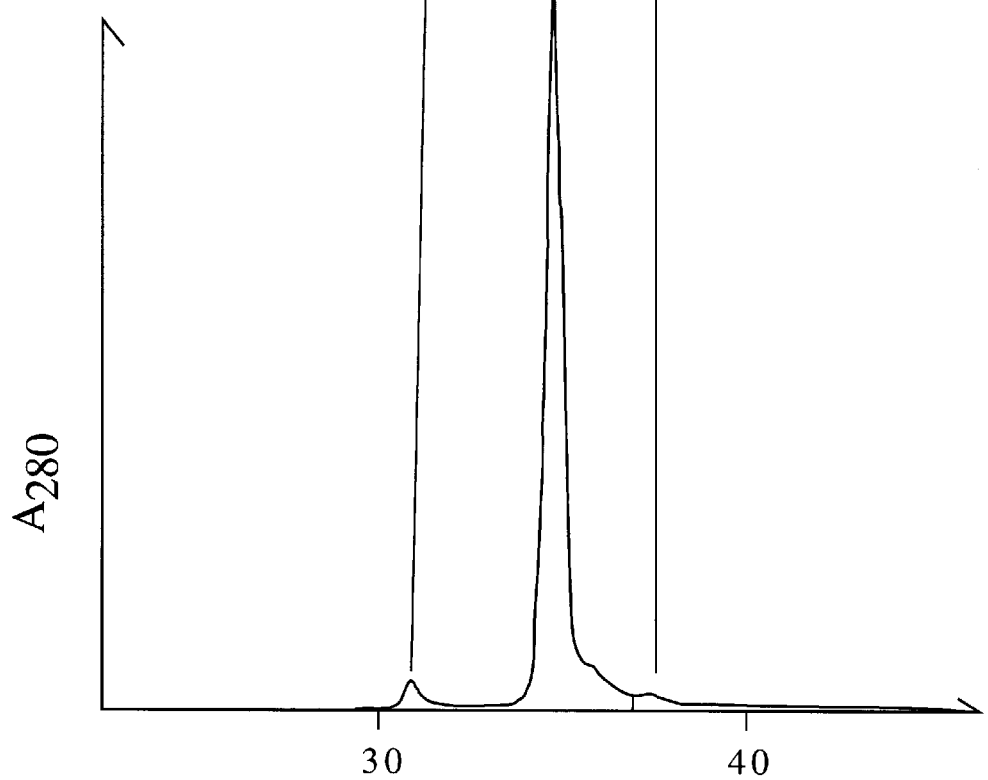

Pro-MSP and pro-C672A, having been subjected to the above-mentioned kallikrein treatment, were each loaded onto Phenyl 5PW reverse phase column, eluted with water/acetonitrile gradient, while monitoring absorption at 280 nm (FIG. 4). SDS-PAGE under reducing condition of each eluted fraction exhibited the elution of the α-chain, the two-chain form, and the β-chain, in this order. Beside each of the main peaks of the α-chain and the two-chain form, minor peaks were observed which presumably occurred by differences in the elution positions due to the difference in sugar chain composition. Specifically, the amino acid sequence of MSP has three putative glycosylation sites: two sites in α-chain and one site in the β-chain. Thus, while the β-chain peak showed a relatively simple pattern, the α-chain peak and the two-chain form peak showed rather complicated patterns. The ratio between the areas of the α-chain, the two-chain form, and the β-chain was determined to be 26:58:16 in the case of the recombinant protein of native form MSP. In the case of the C672A variant, the ratio was 7:88:5, indicating a significant decrease in the free-chain component Although there are some recombinant native form MSPs wherein the α-chain is not cross-linked to the β-chain via a disulfide bond, substituting the cysteine at position 672 with alanine remarkably enhanced the cross-linking, as shown in FIG. 4. Based on the comparison with plasminogen, the α-chain cross-links with the β-chain through a disulfide bond between Cys (468) and Cys (588), but Cys (588) presumably formed a disulfide bond with Cys (672) within the same β-chain in some recombinant proteins.

Evaluation of macrophage stimulating activity

The chemotaxis stimulating activity of the above-mentioned C672A variant on murine peritoneal macrophages was evaluated according to the method described in Skeel et al. (Skeel et al. J. Exp. Med., 173, 1227(1991)).

Specifically, a cold serum-free RPMI medium was injected into a C3H/HeN mouse (Charles River) intraperitoneally, and thereafter was recovered in order to collect resident peritoneal macrophages therein. The chemotaxisic response was measured by using a multi-well chemotaxis chamber as follows: First, serum-free RPMI medium was added in the bottom chamber, on which a polycarbonate membrane (with pores having a diameter of 5 μm) was placed as a partition. An upper chamber was filled with 120,000 macrophages suspended in the same medium and native MSP or the C672A variant diluted at an appropriate concentration. After incubation for 3.5 hours at 37° C., the filter was washed with water and the cells attached to the upper side of the filter were mechanically removed using a rubber policeman. After the filter was dried, the cells were stained with Diff-Quik. The number of the cells on the lower side of the filter was counted by using an image analyzer. Thus, the ratio (%) of the number of cells on the lower side to the cells added to the upper chamber was determined.

Figure 5:
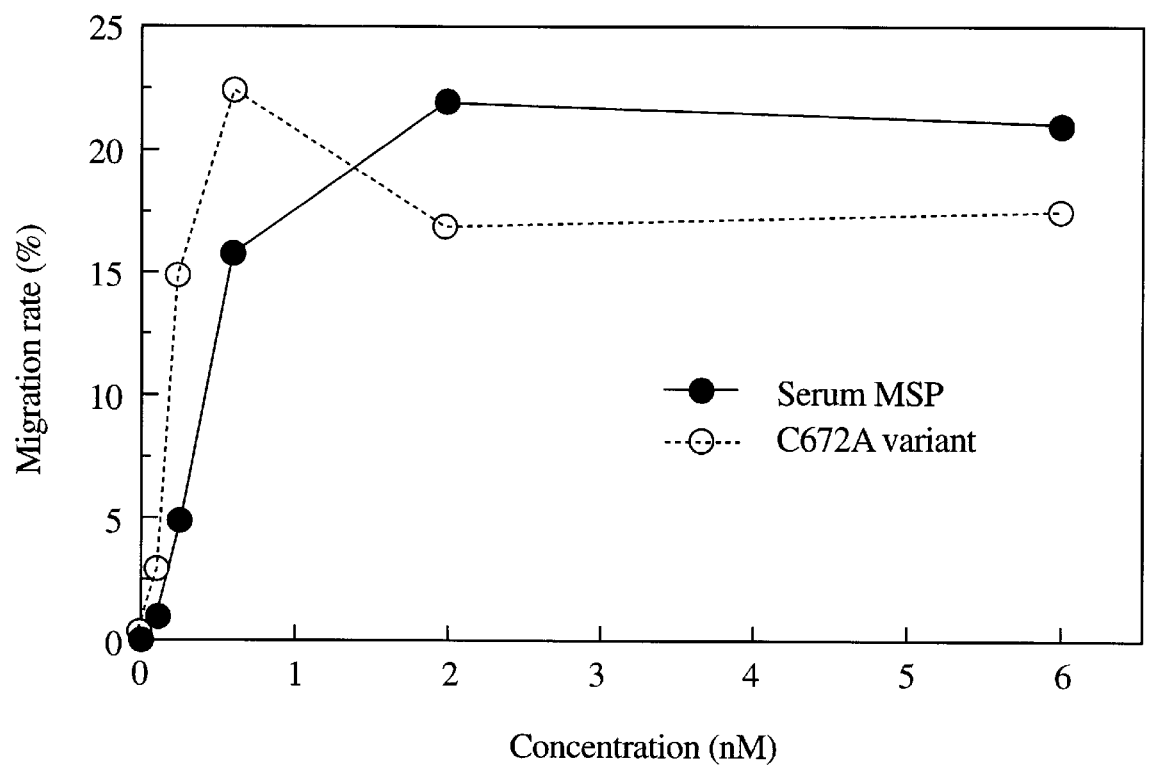
FIG. 5 is a graph showing the chemotaxis-stimulating activity of MSP purified from human serum and C672A variant on murine peritoneal macrophages.

FIG. 5 shows a comparison between the above-mentioned C672A variant (obtained by activating purified pro-C672A variant by kallikrein treatment) and native MSP purified from human serum by the method described in the above literature. As seen from FIG. 5, the C672A variant retained substantially the same level of physiological activity as that of native MSP. That is, the biological activity of C672A was retained after the substitution of cysteine at position 672 with alanine, which is not found at the same position as in native MSP.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A macrophage stimulating protein variant of SEQ ID NO:1, wherein the cysteine residue at position 672 from the N-terminus of SEQ ID NO:1 is deleted or substituted by another amino acid residue.

2. The macrophage stimulating protein variant according to claim 1, wherein the cysteine residue is deleted.

3. The macrophage stimulating protein variant according to claim 1, wherein the cysteine residue is substituted by another amino acid residue.

4. A DNA fragment encoding a macrophage stimulating variant of SEQ ID NO:1, wherein the cysteine residue at position 672 from the N-terminus of SEQ ID NO:1 is deleted or substituted by another amino acid residue.

5. The DNA fragment encoding a macrophage stimulating protein variant according to claim 4, wherein the cysteine residue is deleted.

6. A DNA fragment encoding a macrophage stimulating protein variant according to claim 5, wherein nucleotides at positions 2014 to 2016 of SEQ ID NO: 2 are deleted.

7. The DNA fragment encoding a macrophage stimulating protein variant according to claim 4, wherein the another amino acid is an alanine residue.

8. The DNA fragment encoding a macrophage stimulating protein variant according to claim 4, wherein nucleotides at positions 2014 to 2016 of SEQ ID NO: 2 are substituted by other nucleotides.

9. The DNA fragment encoding a macrophage stimulating protein variant according to claim 8, wherein the other nucleotides are GCC, GCU, GCA or GCG.

10. A recombinant vector comprising the DNA fragment of claim 4.

11. A host cell transformed with the recombinant vector of claim 10.

12. A method for producing a macrophage stimulating protein variant of SEQ ID NO:1, comprising the steps of:

culturing the transformed host cell of claim 11; and recovering the macrophage stimulating protein variant from the culture.

13. The method for producing a macrophage stimulating protein variant according to claim 12, wherein the cysteine residue is deleted.

14. The method for producing a macrophage stimulating protein variant according to claim 12, wherein the cysteine residue is substituted by another amino acid residue.

* * * * *

UNITED STATES PATENT AND TRADEMARK OFFICE
CERTIFICATE OF CORRECTION

PATENT NO.    :  5,916,770
DATED         :  June 29, 1999
INVENTOR(S)   :  Yoshikawa et al.

It is certified that errors appear in the above-identified patent and that said Letters Patent is hereby corrected as shown below:

In Column 1, Line 52: "form The" should read --form. The--.

In Column 3, Line 4: "quantity" should read --quantity.--.

In Column 3, Line 57: "chaperone The" should read --chaperone. The--.

In Column 4, Line 41: "Cys(56$^2$)" should read --Cys(562)--.

In Column 5, Line 15: "1 The" should read --1. The--.

In Column 8, Line 16: "16 kb" should read --1.6 kb--.

In Column 9, Line 33: "transformed The" should read --transformed. The--.

In Column 9, Line 40: "dialysis The" should read --dialysis. The--.

In Column 9, Line 43: "plates Thereafter" should read --plates. Thereafter--.

In Column 10, Line 6: "respectively)" should read --respectively).--

In Column 10, Line 13: "passed The" should read --passed. The--.

In Column 10, Line 18: "treatment Afterward" should read --treatment. Afterward--.

UNITED STATES PATENT AND TRADEMARK OFFICE
CERTIFICATE OF CORRECTION

PATENT NO.   :   5,916,770
DATED        :   June 29, 1999
INVENTOR(S)  :   Yoshikawa et al.

It is certified that errors appear in the above-identified patent and that said Letters Patent is hereby corrected as shown below:

In Column 10, Line 20: "appeared That" should read --appeared. That--.

In Column 10, Line 50: "component Although" should read --component. Although--.

IN THE CLAIMS

In Claim 6, Column 22, Line 57: "A" should read --The--.

Signed and Sealed this

Fourteenth Day of December, 1999

Q. TODD DICKINSON

*Attest:*

*Attesting Officer*    *Acting Commissioner of Patents and Trademarks*